United States Patent [19]

Isbister

[11] Patent Number: 5,770,395
[45] Date of Patent: *Jun. 23, 1998

[54] BIOLOGICAL ASSAY FOR MICROBIAL CONTAMINATION

[75] Inventor: Jenefir D. Isbister, Potomac, Md.

[73] Assignee: Center for Innovative Technology, Herndon, Va.

[ * ] Notice: The term of this patent shall not extend beyond the expiration date of Pat. No. 5,550,032.

[21] Appl. No.: 665,537

[22] Filed: Jun. 18, 1996

Related U.S. Application Data

[63] Continuation of Ser. No. 250,383, May 27, 1994, Pat. No. 5,550,032.

[51] Int. Cl.⁶ .................................................. C12Q 1/06
[52] U.S. Cl. .............................................. 435/39; 435/39
[58] Field of Search ................................... 435/4, 29, 34, 435/39

[56] References Cited

U.S. PATENT DOCUMENTS

| | | |
|---|---|---|
| 3,881,993 | 5/1975 | Freake et al. . |
| 4,083,852 | 4/1978 | Terasawa et al. . |
| 4,299,916 | 11/1981 | Litman et al. . |
| 4,366,241 | 12/1982 | Tom et al. . |
| 4,391,904 | 7/1983 | Litman et al. . |
| 4,533,629 | 8/1985 | Litman et al. . |
| 4,540,659 | 9/1985 | Litman et al. . |
| 4,610,961 | 9/1986 | Guardino et al. . |
| 4,717,660 | 1/1988 | Schulte . |
| 4,843,000 | 6/1989 | Litman et al. . |
| 4,849,338 | 7/1989 | Litman et al. . |
| 4,912,036 | 3/1990 | Cichanowicz et al. ................... 435/34 |
| 4,923,804 | 5/1990 | Ley et al. .................................. 435/38 |
| 4,925,789 | 5/1990 | Edberg ...................................... 435/38 |
| 4,945,060 | 7/1990 | Turner et al. ........................... 435/291 |
| 4,956,301 | 9/1990 | Ismail et al. . |
| 5,039,349 | 8/1991 | Schoeppel ................................. 134/26 |
| 5,156,953 | 10/1992 | Litman et al. . |
| 5,159,799 | 11/1992 | Rising et al. ............................. 53/433 |
| 5,196,313 | 3/1993 | Culbreth .................................. 435/32 |
| 5,206,151 | 4/1993 | Robertson ................................ 435/32 |
| 5,366,873 | 11/1994 | Eden etal. ................................ 435/34 |
| 5,420,017 | 5/1995 | Tuompo et al. ......................... 435/29 |
| 5,550,032 | 8/1996 | Isbister .................................... 435/39 |

OTHER PUBLICATIONS

Grabherr, G. et al., Biological Abstract #79:173371, Oecol. Plant 13(3) pp. 227–252 (1978).

Davis et al. *Microbiology*, Harper & Row (1980) pp. 65, 67, 114.

*Primary Examiner*—John Kight
*Assistant Examiner*—Dameron Jones
*Attorney, Agent, or Firm*—Whitham, Curtis, Whitham & McGinn

[57] ABSTRACT

Methods and kits for detecting the presence of and quantifying the concentration of viable microorganisms in a liquid sample are provided. Enzymes present in viable microorgansims reduce an indicator reagent to produce a visible color change. No titrations or dilutions of the sample are necessary. Variations of the test are described which can be used to detect a threshold level of viable microorganisms, to detect the presence or absence of viable microorganisms and to quantify the concentration of viable microorganisms in a liquid sample. The results are obtained rapidly with those for the detection available within thirty minutes and those for the quantification available within thirteen hours.

20 Claims, 2 Drawing Sheets

BIOLOGICAL ASSAY FOR MICROBIAL CONTAMINATION

CROSS REFERENCE TO RELATED APPLICATION

This application is a continuation of application Ser. No. 08/250,383 filed May 27, 1994, U.S. Pat. No. 5,550,032.

DESCRIPTION

BACKGROUND OF THE INVENTION

1. Field of the Invention

This invention generally relates to a method for rapidly and inexpensively determining the presence or absence and level or concentration of microbial contaminants in a liquid sample. More particularly, the invention provides a simplified assay which includes an indicator compound which visibly changes color upon reduction. This assay is particularly useful in detecting microbial contamination in cooling water towers, drinking water, food processing operations, medical laboratories, and other industrial processes.

2. Description of the Prior Art

The contamination of liquid, especially water, with microorganisms can be a major problem in a variety of industrial applications, for example delivery and production of drinking water, food processing operations, medical laboratory processes and industrial cooling towers. The presence of the microorganisms can be dangerous to the health of the population and can also result in damage to industrial processing equipment. Therefore, it is recommended that frequent testing be conducted to detect the presence and/or concentration of microbial contaminants.

The techniques currently in use require approximately 24 to 72 hours to assess the contaminants in the liquid sample. In addition, the results of the testing may be difficult to interpret or quantify. Often, specialized equipment is required to analyze or obtain the results of the testing. Furthermore, the tests are often expensive. As a result of the problems and complications with the current methods of testing, the recommended amount of testing is not completed. Moreover, due to the extensive length of time required to obtain the results, the data will not accurately represent the conditions at the time the test results are determined and often inadequate or improper treatment will occur.

An assay which detects a threshold level of microbial contamination is particularly useful in assessing water in cooling towers. Industrial cooling towers are commonly used to reduce and dissipate heat generated from industrial processes. It is common, especially in warm temperature conditions, for biofilms to form on the pipes from bacteria and the like. The biofilms reduce the heat exchange which occurs between the fluid in the pipes and the cooling tower water. The inadequate cooling by the cooling tower water results in an elevated process liquid temperature which can lead to damage to the process equipment. Therefore, it is necessary to reduce bacterial contamination to a manageable level. However, the addition of excess quantities of biocides or bacterial growth inhibitors is not desirable due to the environmental impact, the high cost of the chemicals and the difficulties in disposing of the water which has been treated. Therefore, it is important to rapidly determine a threshold level of contamination, so that an appropriate treatment course can be followed.

U.S. Pat. No. 5,206,151 to Robertson describes a technique which requires multiple dilutions and titrations for determining the minimum amount of biocides or antimicrobial agents necessary to control microbial growth. In addition, the Robertson method requires the addition of nutrient matter to accelerate microbial activity in the contaminated sample.

SUMMARY OF THE INVENTION

It is therefore an object of this invention to provide a new method for rapidly and accurately detecting and indicating the presence of viable microorganisms in a liquid sample.

It is also an object of this invention to provide a method for rapidly and accurately quantifying and indicating the concentration of viable microorganisms in a liquid sample.

It is another object of this invention to provide a method for rapidly and accurately detecting and indicating a threshold concentration of microbial contaminants in a liquid sample.

It is a further object of this invention to provide a method in which the detection is clearly visible to the human eye.

It is also an object of this invention to provide a method which detects the contamination within thirty minutes.

It is another object of this invention to provide a method for rapidly and accurately detecting the presence of microorganisms using the absorption spectra.

It is a further object of this invention to provide a rapid and accurate method for quantitatively detecting and indicating viable microorganisms in a liquid sample by correlating the time required for detection to the number of viable microorganisms.

It is another object of this invention to provide a kit for rapidly and accurately determining and indicating the presence or absence of microbial contamination in a liquid sample.

It is also an object of this invention to provide a kit for rapidly and accurately detecting and indicating a threshold level or the concentration of microorganisms in a liquid sample.

According to the invention, methods and kits are provided for detecting the presence of and quantifying the concentration of viable microorganisms in a liquid sample. An indicator reagent which undergoes a visible color change when it is reduced is used. Only viable microorganisms can reduce the indicator; dead microorganisms have no effect. Variations of the basic procedure can be used respectively to detect a threshold level of viable microorganisms, to detect the presence or absence of viable microorganisms and to quantify the concentration of viable microorganisms in a liquid sample.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
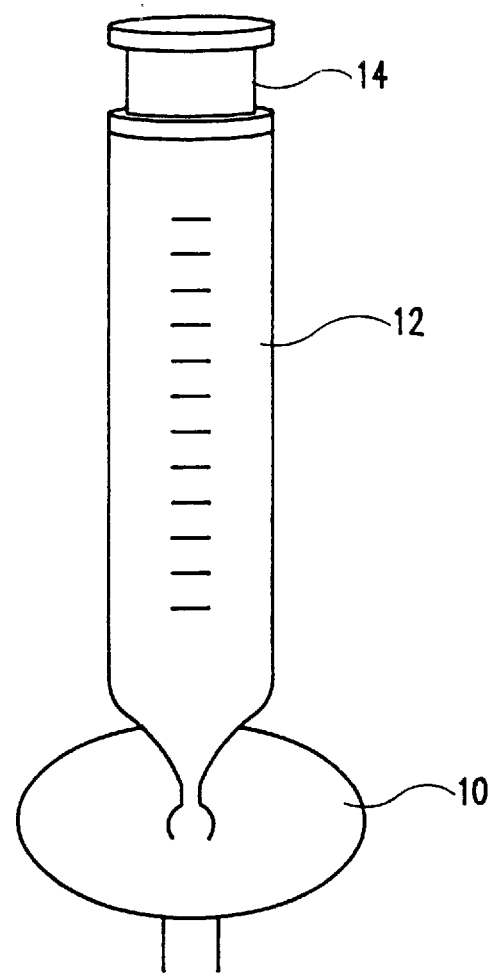
FIG. 1 is a side view of a kit, including a vessel, and a filter according to a first embodiment of this invention.

New techniques for rapidly and accurately detecting microbial contamination in a liquid have been discovered.

These techniques are useful for any application in which it is necessary to have clean water, for example in drinking water, food processing, medical laboratories and cooling towers.

A threshold level of viable microorganisms in a liquid can be detected by directing the liquid through a filter which is of a size capable of trapping and concentrating the microorganisms on the filter media, e.g. 0.1–0.5 $\mu$m porosity, with 0.2 $\mu$m preferred. It is preferred that a polysulfone or similar filter be used. Particularly good polysulfone filters for the practice of the invention are the Gelman Acrodisc Syringe Filters available from Baxter Scientific. Filters made from polypropylene or cellulose do not achieve optimum results and are thought to inhibit the reduction of the indicator compound by the microorganisms.

After the liquid is directed through the filter, an indicator solution is applied to the filter. It is preferred that the indicator solution include an indicator compound which undergoes a visible color change upon reduction. It is preferred that the indicator compound is triphenyltetrazolium chloride (TPTZ).

It has been found that between approximately 1.25 and 5 milligrams of TPTZ per filter is necessary for threshold determination within thirty minutes. It is most preferred to use a concentration of between approximately 2 and 3 milligrams of TPTZ on the filter.

It is also preferred that the indicator solution additionally contain a proteinaceous material and an alcohol. With regard to the alcohol, it has been found that ethanol, when present at less than 10% by volume produces the best results. However, other alcohols can be used. The low concentration of alcohol alters the permeability of the cell allowing more rapid reduction of the indicator but does not inhibit microbial metabolism. Too high an alcohol concentration will kill the microorganisms; thus nullifying the test results. It has been found that water alone is ineffective as a carrier.

The proteinaceous material can be any general culture broth and serves the function of protecting the cellular integrity of the microorganisms. The culture broths can include AC broth; protease peptone broth; brain heart infusion broth; nutrient broth and tryptic soy broth (TSB). It is preferred that the protein material is TSB. The carrier combination of ethanol and TSB has been found to be optimal and it is thought that this is because the proteins in the TSB protect the cells while the ethanol alters the permeability of the cells.

The indicator compound detects, within thirty minutes, a threshold level of $10^6$ colony forming units (CFU)/mL of viable microorganisms. If TPTZ is used as the indicator compound, the microorganisms reduce the TPTZ to formazan which produces a "pink" color on the filter paper. Alternate threshold levels of microorganisms may be detected by varying the volume of the water sample which is applied to the filter. In addition, if a different indicator compound is used, it is understood that indication of viable microorganisms may produce different indicia of the results. It should be noted that there is no need with this technique to enhance or amplify the microorganisms. Furthermore, the compounds used have a shelf life of at least one year.

A representative configuration for the apparatus for performing the assay or for use in a kit is shown in FIG. 1. A vessel, such as a syringe or tube 12 is fitted with a plunger or other mechanism 14. The plunger or other mechanism 14 is used to draw a measured volume of the sample into the vessel reservoir. The vessel is then fitted with an appropriate sized filter 10. The filter is generally removable from the vessel. The plunger or other mechanism 14 is used to force the sample through the filter thereby depositing the microorganisms contained in the sample on the filter. It is also contemplated that a vacuum in the vessel can force the sample into the vessel.

The following example demonstrates the speed and accuracy of the results which can be obtained using the technique described supra. In this example, a 20 mL sample of water was drawn into a syringe with a Luer loc tip. A filter is fitted onto the end of the syringe at the Luer loc tip. The water is then forced through the filter using the plunger of the syringe. Three drops of indicator mixture is introduced onto the filter using a syringe, a medicine dropper or other similar means. The indicator mixture contains 17 mg of TPTZ in 0.975 mL of TSB with 0.025 mL of 95% ethanol. Three drops of the indicator mixture contains approximately 2.5 mg of TPTZ.

The indicator mixture must flood the surface of the filter. The time that the indicator mixture is applied to the filter is noted and recorded. After thirty minutes, the test filter is examined for a pink color and is compared to a negative control which can be an unused filter. The pink color is a positive test result which indicates that the water sample contains $\geq 1 \times 10^6$ CFU/mL. The results at thirty minutes indicate whether the concentration of microorganisms is at the threshold level. Four groups of tests were performed with the results summarized in Table 1.

TABLE 1

| Test number | Titer | Reaction |
| --- | --- | --- |
| 1 | $1.5 \times 10^6$ cfu/mL | +(immediately) |
| 2 | $1.5 \times 10^5$ cfu/mL | −(30 minutes) |
| 3 | $1.5 \times 10^6$ cfu/mL | +(5 minutes) |
| 4 | $1.5 \times 10^6$ cfu/mL | +(5 minutes) |
| 5 | $1.5 \times 10^3$ cfu/mL | −(30 minutes) |
| 6 | $2 \times 10^6$ cfu/mL | +(15 minutes) |
| 7 | $2 \times 10^5$ cfu/mL | −(30 minutes) |
| 8 | $2 \times 10^4$ cfu/mL | −(30 minutes) |
| 9 | $2 \times 10^3$ cfu/mL | −(30 minutes) |
| 10 | $1.3 \times 10^6$ cfu/mL | +(15 minutes) |
| 11 | $1.3 \times 10^5$ cfu/mL | −(30 minutes) |
| 12 | $1.3 \times 10^7$ cfu/mL | +(15 minutes) |

Other standard reduction oxidation indicators can be used in the practice of the invention. Some representative redox indicators are aniline blue black (naphthol blue black); benzopurpurin 48; 2,6-Dibromoquninone-chlorimide; 2,6-dichloroindophenol, sodium salt; diphenylamine; diphenylaminesulfonic acid, sodium salt; erioglaucine; indigo carmine; janus green; methylene blue; neutral red; Nile blue A; o-phenanthroline; safranin O; sodium diphenylaminesulfonate; tartrazine; thionin; o-Tolidine; xylene cyanol FF; and tetrazolium compounds.

Figure 2:
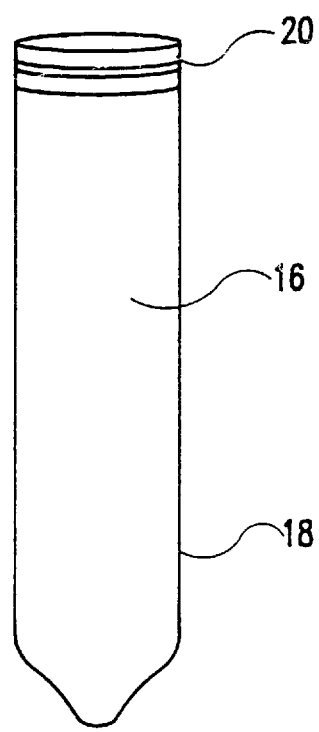
FIG. 2 is a side view of a kit for use in quantifying the number of microorganisms in accordance with a second and third embodiment of this invention.

It is also possible using a similar technique to quantitatively determine the concentration of viable microorganisms in a water sample within a thirteen hour period. A large concentration range can be determined and it is possible to determine a concentration even if less than 10 cfu/mL are present. Similar to the technique discussed above, a water sample (5 mL) is placed in each of two sterile test tubes which may contain a dry nutrient formulation. A representative example of a vessel which can be used in the practice of this invention is shown in FIG. 2. As seen, a tube or vessel 18 contains a liquid sample and a nutrient formulation 16. The nutrient formulation can be any general nutrient composition as is noted, supra. The nutrient formulation, preferably TSB, should be present in the amount of 20–30 mg/mL of sample. A cap or other sealing mechanism 20 is applied to the tubes and the tubes are thoroughly mixed by inverting and shaking. In one tube, which is the test, one drop, or approximately 0.25–1 mg of indicator solution, preferably TPTZ is added to the water and nutrient mixture per mL of sample. The indicator solution includes TPTZ at a concentration of 50 mg/mL in sterile saline or sterile distilled water. This results in approximately 2.5 mg of TPTZ being delivered into each tube which contains a water sample to be tested. It should be noted that, as discussed above, other redox indicators might be used. The other tube is the control and contains the water 10 sample but does not contain indicator solution, i.e. TPTZ.

Figure 3:
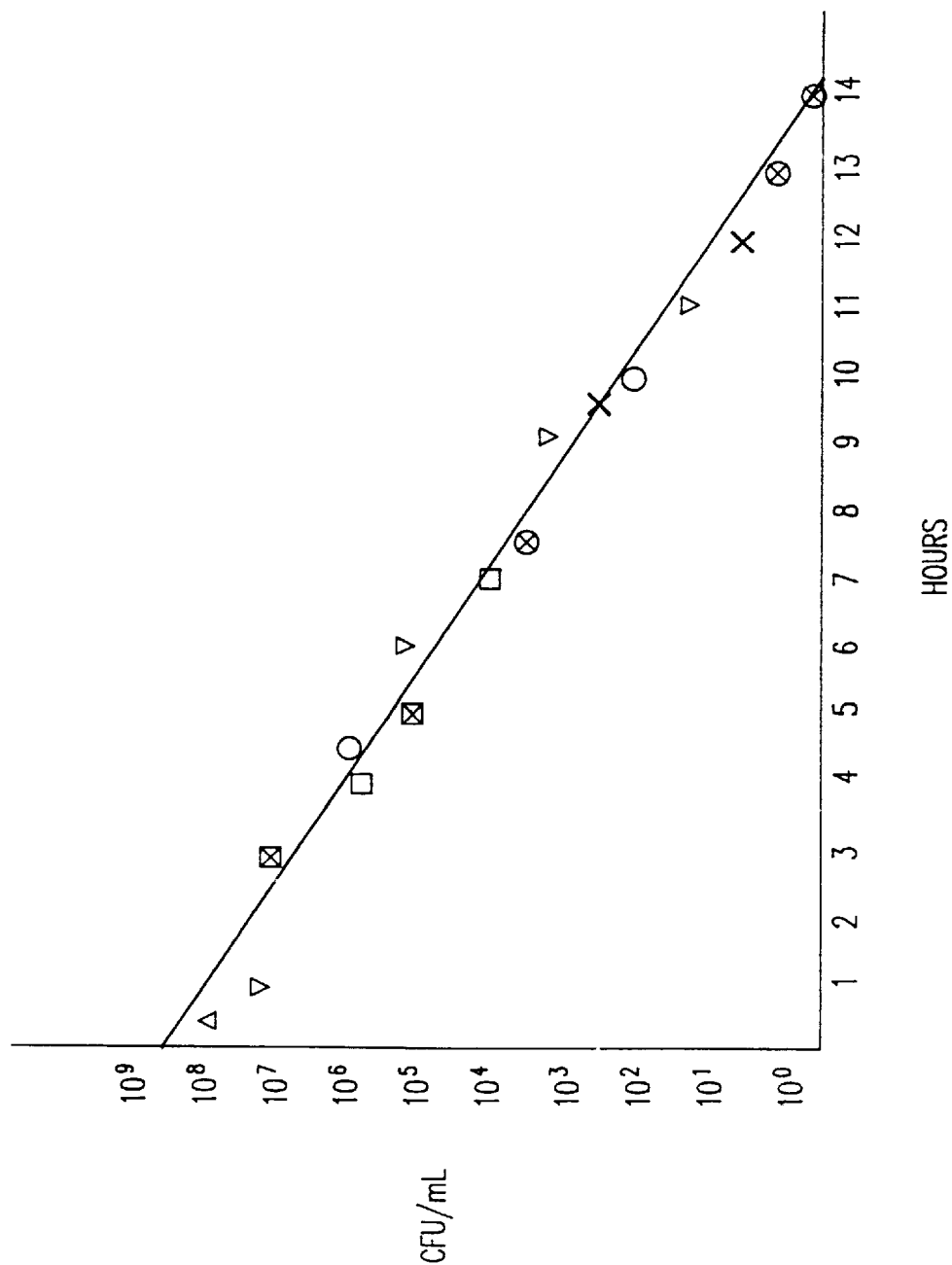
FIG. 3 is a graph of the correlation between time and concentration of microorganisms.

At this point, the tubes should be incubated at or near 35° C. It has been found that this can be accomplished by placing the tubes in the pocket of the individual performing the test or by placing them in a is heat block or incubator, if one is available. The samples are visually compared at predetermined intervals, preferably every hour until a pink color is visible to the human eye. It is known that if a different indicator reagent is used, the reduction by the microorganisms will produce a result which corresponds to the properties of the reagent. It has been found that the time required for the replication of the microorganisms in the sample to a critical mass sufficient to reduce the indicator and generate a pink color can be correlated to the initial microbial concentration in the water sample. A representative plot of correlation between time and initial concentration of viable microorganisms is shown in FIG. 3.

It is also contemplated that a kit can be provided which includes the solution in a dried form. This kit could be similar to those described in U.S. Pat. No. 5,159,799, which has been incorporated by reference. As described therein, the kit includes a collecting container with a means for breaking the tip. A vacuum causes a sample to be drawn into the container.

It is also possible to use the techniques described supra to detect the presence or absence of viable microorganisms in a water sample from the absorption spectra. The method is similar to those described above, however, the sample is place in a vessel which can be used in an absorbance measurement device. It is contemplated that the vessel can be a UV/Vis cuvette. The cuvette should be sterilized or thoroughly sanitized, for example by rinsing with 95% ethanol, prior to the addition of the water sample. Two drops (approximately 100 µl of a solution which contains 50 mg TPTZ/mL in 95% ethanol) of TPTZ indicator solution, approximately 2.5 to 5 mg of TPTZ, is delivered into a 2 mL water sample which is to be tested. An absorbance measurement is then made in the 200 to 300 nm range. The optimal absorption measurement is at 254 nm. The TPTZ will not absorb in this range unless it has been reduced. Only viable microorganisms will reduce TPTZ. Therefore, the presence of microorganisms will result in a reduction of TPTZ such that their presence is detected by the absorption spectra. It has been shown that as few as one microorganism/mL in a liquid sample can be detected using this technique.

While the invention has been described in terms of its preferred embodiments, those skilled in the art will recognize that the invention can be practiced with modification within the spirit and scope of the appended claims.

I claim:

1. A method for detecting the presence or absence of a predetermined minimum level of viable microorganisms in a liquid sample within thirty minutes, comprising the steps of:

introducing a liquid sample through a polysulfone filter capable of trapping microorganisms on said filter;

applying an indicator solution including an indicator compound, said indicator compound including a triphenyltetrazolium indicator which undergoes a visible color change upon reduction on said polysulfone filter after said introducing step; and determining the presence or absence of a clearly visible color change on said filter within approximately thirty minutes.

2. A method, as recited in claim 1 wherein said indicator compound is dispersed in a liquid mixture which includes proteinaceous material and an alcohol.

3. A method, as recited in claim 2, wherein said polysulfone filter has a pore size no greater than 0.2 µm.

4. A method, as recited in claim 2, wherein said indicator compound in said indicator solution is triphenyltetrazolium chloride.

5. A method, as recited in claim 2, wherein said proteinaceous material in said indicator solution is trypticase soy broth.

6. A method, as recited in claim 2, wherein said alcohol in said indicator solution is ethanol at a concentration of less than approximately 10% by volume of said indicator solution.

7. The method of claim 1, wherein said polysulfone filter has a pore size ranging from 0.1 to 0.5 µm.

8. The method of claim 1, wherein said predetermined minimum level of viable microorganisms is $10^6$ colony forming units of viable microorganisms per mL of said liquid sample.

9. The method of claim 1, wherein said step of introducing a liquid sample through a polysulfone filter comprises using external pressure to pass said liquid sample through the polysulfone filter so as to retain the microorganisms on the surface of the filter.

10. The method of claim 1, further comprising the steps of: prior to said step of introducing said liquid sample through said filter, providing a vessel having an open end and an opposite end fitted with a plunger, introducing a volume of said liquid sample into said vessel, fitting said filter onto said open end of said vessel, and said step of introducing said liquid sample through said filter being accomplished by using said plunger to force said liquid sample through said filter.

11. A method for determining the concentration of viable microorganisms in a liquid, comprising the steps of:

selecting a sample of said liquid from a source where contamination is suspected;

mixing said liquid with an indicator compound inside a vessel, said indicator compound being one which undergoes a visible color change upon reduction as a result of contact with a viable microorganism;

visually detecting a predetermined visible color change in said liquid sample due to said viable microorganisms being in contact with said indicator compound;

measuring an elapsed time for said predetermined visible color change to occur in said liquid sample, said elapsed time indicating the concentration of viable microorganisms in said liquid at the time of selection of said sample.

12. The method of claim 11 wherein said step of measuring an elapsed time for said predetermined color change includes the steps of:

periodically comparing said liquid sample in said vessel from a time said indicator compound is mixed therewith with a control liquid sample contained in a second vessel, wherein said control liquid sample is devoid of said indicator compound, until said predetermined visual color change is observed in said liquid sample including said indicator compound by comparison to said control sample devoid of said indicator compound.

13. The method of claim 12 further comprising the step of incubating said vessel containing said liquid sample and said second vessel containing said control liquid sample.

14. A method, as recited in claim 11 wherein said step of measuring an elapsed time for said predetermined visible color change includes the step of comparing said liquid sample in said vessel with a standard.

15. A method, as recited in claim 8 wherein said liquid sample is water.

16. A kit for detecting concentration of viable microorganisms in a liquid sample, comprising:

a container for holding a liquid sample;

an indicator compound being one which undergoes a visible color change upon reduction as a result of contact with a viable microorganism, said indicator compound being positionable within said container;

means for visually detecting said visible color change of said indicator compound;

means for measuring a period of time during which said visible color change of said indicator compound will occur in said container; and means for determining a concentration of viable microorganisms in said liquid sample from said period of time measured by said means for measuring.

17. The kit as recited in claim 16 wherein said means for determining includes a second container for holding a control liquid sample wherein said control liquid sample is identical to said liquid sample with the proviso that said second container contains none of said indicator compound, whereby said time of change is determined by comparing said liquid sample in said container with said control liquid sample in said second container.

18. The kit of claim 16, wherein said container for holding a liquid sample is a tube.

19. The kit of claim 17, wherein said second container for holding a control liquid sample is a tube.

20. A kit, as recited in claim 16 wherein said liquid sample is water.

* * * * *